(12) United States Patent
Bareau et al.

(10) Patent No.: US 10,940,299 B2
(45) Date of Patent: Mar. 9, 2021

(54) CENTER MARKER FOR DILATATION BALLOON

(71) Applicant: GYRUS ACMI, INC., Southborough, MA (US)

(72) Inventors: Jane Bareau, Needham, MA (US); Jeremy DiTullio, Worcester, MA (US); Erica Matthes, Waltham, MA (US)

(73) Assignee: Gyms Acmi, Inc., Southborough, MA (US)

( * ) Notice: Subject to any disclaimer, the term of this patent is extended or adjusted under 35 U.S.C. 154(b) by 541 days.

(21) Appl. No.: 14/955,453

(22) Filed: Dec. 1, 2015

(65) Prior Publication Data

US 2017/0043142 A1 Feb. 16, 2017

Related U.S. Application Data

(60) Provisional application No. 62/202,984, filed on Aug. 10, 2015.

(51) Int. Cl.
*A61M 29/02* (2006.01)
*A61M 25/10* (2013.01)
*A61B 1/00* (2006.01)
*A61B 1/018* (2006.01)
*A61B 1/273* (2006.01)
*A61B 1/31* (2006.01)

(52) U.S. Cl.
CPC ......... *A61M 29/02* (2013.01); *A61B 1/00082* (2013.01); *A61B 1/018* (2013.01); *A61M 25/10* (2013.01); *A61M 25/104* (2013.01); *A61B 1/2736* (2013.01); *A61B 1/31* (2013.01); *A61M 2025/1079* (2013.01); *A61M 2029/025* (2013.01)

(58) Field of Classification Search
CPC .... A61M 25/10; A61B 1/00082; A61B 1/018; A61B 1/2736
See application file for complete search history.

(56) References Cited

U.S. PATENT DOCUMENTS

| 5,021,043 A | 6/1991 | Becker et al. |
| 5,156,594 A | 10/1992 | Keith |
| 5,169,386 A | 12/1992 | Becker et al. |

(Continued)

FOREIGN PATENT DOCUMENTS

| CN | 1630542 A | 6/2005 |
| CN | 103282075 A | 9/2013 |

(Continued)

OTHER PUBLICATIONS

Japanese Office Action for Japanese Application 2018-500725, dated Jul. 3, 2019.

(Continued)

*Primary Examiner* — Julie A Szpira
(74) *Attorney, Agent, or Firm* — Schwegman Lundberg & Woessner, P.A.

(57) ABSTRACT

The present invention is premised upon an improved balloon dilator, more particularly to an improved balloon dilator comprising an expandable balloon, a core wire which extends through the expandable balloon, and a single visual marker band positioned at a geometric center within the balloon dilator which may selectively reflect certain wavelengths of light.

15 Claims, 10 Drawing Sheets

(56) References Cited

U.S. PATENT DOCUMENTS

| | | |
|---|---|---|
| 5,320,604 A | 6/1994 | Walker et al. |
| 5,411,016 A * | 5/1995 | Kume ................ A61B 1/00082 |
| | | 600/114 |
| 5,423,755 A | 6/1995 | Kesten et al. |
| 5,474,537 A | 12/1995 | Solar |
| 5,643,209 A | 7/1997 | Fugoso et al. |
| 5,779,673 A * | 7/1998 | Roth ................ A61M 25/1011 |
| | | 604/101.03 |
| 5,797,878 A | 8/1998 | Bleam |
| 5,961,510 A | 10/1999 | Fugoso et al. |
| 6,146,409 A * | 11/2000 | Overholt ............. A61N 5/0601 |
| | | 607/88 |
| 6,179,811 B1 | 1/2001 | Fugoso et al. |
| 6,251,094 B1 | 6/2001 | Bleam |
| 6,488,653 B1 | 12/2002 | Lombardo |
| 6,520,934 B1 | 2/2003 | Lee et al. |
| 6,733,487 B2 | 5/2004 | Keith et al. |
| 6,761,708 B1 | 7/2004 | Chiu et al. |
| 6,953,431 B2 | 10/2005 | Barthel |
| 7,641,668 B2 | 1/2010 | Perry et al. |
| 7,678,068 B2 | 3/2010 | Levine et al. |
| 7,785,315 B1 | 8/2010 | Muni et al. |
| 8,034,022 B2 | 10/2011 | Boatman |
| 8,123,722 B2 | 2/2012 | Chang et al. |
| 8,157,765 B2 | 4/2012 | Adams et al. |
| 8,298,134 B2 | 10/2012 | Barthel |
| 8,388,642 B2 | 3/2013 | Muni et al. |
| 8,475,360 B2 | 7/2013 | Brown |
| 8,562,560 B2 | 10/2013 | Adams et al. |
| 9,095,646 B2 * | 8/2015 | Chow ................... A61B 17/24 |
| 2003/0015284 A1 * | 1/2003 | Merdan ................. A61L 29/14 |
| | | 156/272.2 |
| 2003/0018353 A1 * | 1/2003 | Yang ................. A61M 25/0045 |
| | | 606/194 |
| 2006/0004323 A1 | 1/2006 | Chang et al. |
| 2006/0135962 A1 * | 6/2006 | Kick ................... A61B 17/3478 |
| | | 606/108 |
| 2008/0232963 A1 | 9/2008 | Durocher et al. |
| 2010/0010302 A1 * | 1/2010 | Hadani .............. A61B 1/00101 |
| | | 600/109 |
| 2010/0087732 A1 * | 4/2010 | Eberle ................ A61B 5/0097 |
| | | 600/437 |
| 2011/0160661 A1 * | 6/2011 | Elton .................... A61M 25/10 |
| | | 604/103.06 |
| 2012/0035437 A1 * | 2/2012 | Ferren .................... A61B 1/041 |
| | | 600/302 |
| 2012/0245521 A1 * | 9/2012 | Gulachenski ..... A61M 25/0045 |
| | | 604/103.09 |
| 2013/0184568 A1 * | 7/2013 | Muni .................... A61M 16/04 |
| | | 600/424 |
| 2014/0018732 A1 | 1/2014 | Bagaoisan et al. |
| 2014/0031800 A1 * | 1/2014 | Ben Oren ...... A61B 17/320016 |
| | | 606/7 |
| 2014/0031852 A1 | 1/2014 | Edgren et al. |
| 2015/0112257 A1 * | 4/2015 | Byrne ................... A61M 25/10 |
| | | 604/103.02 |
| 2015/0165170 A1 * | 6/2015 | Beasley .............. A61M 25/104 |
| | | 604/103.1 |
| 2015/0182725 A1 | 7/2015 | Finger et al. |

FOREIGN PATENT DOCUMENTS

| | | |
|---|---|---|
| CN | 103930148 A | 7/2014 |
| CN | 107847718 A | 3/2018 |
| EP | 3307373 A1 | 4/2018 |
| JP | 6142208 A | 2/1986 |
| JP | 542224 A | 2/1993 |
| JP | H5-42224 A | 2/1993 |
| JP | H06142208 A | 5/1994 |
| JP | 10276974 A | 10/1998 |
| JP | H10276974 A | 10/1998 |
| JP | 2003-507096 A | 2/2003 |
| JP | 2008-512212 A | 4/2008 |
| JP | 2008-513125 A | 5/2008 |
| JP | 2014-527858 A | 10/2014 |
| JP | 2018519941 A | 7/2018 |
| WO | 92/03178 A1 | 3/1992 |
| WO | 92/08501 A1 | 5/1992 |
| WO | 92/19311 A1 | 11/1992 |
| WO | 2006/029370 A2 | 3/2006 |
| WO | 2007/020086 A1 | 2/2007 |
| WO | 2012/096816 A1 | 7/2012 |
| WO | 2014/018659 A2 | 1/2014 |
| WO | 2015/102801 A1 | 7/2015 |
| WO | WO-2017027107 A1 | 2/2017 |

OTHER PUBLICATIONS

International Search Report and Written Opinion for International Application No. PCT/US2016/039264; dated Sep. 29, 2016.

"European Application Serial No. 16738934.5, Response filed Oct. 24, 2018", 7 pgs.

"International Application Serial No. PCT/US2016/039264, International Preliminary Report on Patentability dated Feb. 13, 2018", 9 pgs.

"Chinese Application Serial No. 201680041440.9, Office Action dated Feb. 6, 2020", W/ English Translation, 19 pgs.

"Chinese Application Serial No. 201680041440.9, Response Filed Jun. 3, 2020 Office Action dated Feb. 6, 2020", w/ English Claims, 11 pgs.

"Japanese Application Serial No. 2018-500725, Notice of Reason for Rejection dated Nov. 13, 2018", W/ English Translation, 10 pgs.

"Japanese Application Serial No. 2018-500725, Response filed Feb. 8, 2019 to Notice of Reason for Rejection dated Nov. 13, 2018", W/ English Translation, 10 pgs.

"Chinese Application Serial No. 201680041440.9, Office Action dated Sep. 8, 2020", w/ English translation, 14 pgs.

* cited by examiner

CENTER MARKER FOR DILATATION BALLOON

FIELD OF THE INVENTION

The present invention relates to an apparatus and method for balloon dilatation, more particularly for balloon dilation in conjunction with an endoscope.

BACKGROUND

It is well known that dilatation balloons have been used generally to expand tissues inside the body. One such application is esophageal dilatation, which is a therapeutic endoscopic procedure that enlarges the lumen of the esophagus. Esophageal dilatation balloons, or balloon catheters, can be used to treat a number of medical conditions that result from the narrowing of the esophageal lumen, or decreased motility in the esophagus. In another application, balloon catheters may also be used to dilate body passages in angioplasty, angioplasty being a procedure in which a balloon catheter is used to dilate a coronary artery by collapsing or compressing plaque. In yet another application, balloon dilatation of the prostatic urethra may be used to relieve obstruction caused by swelling of the prostate.

During balloon placement, it is critical to center the balloon about an obstruction prior to expansion. Failure to place the balloon about the center of the obstruction may result in longer procedure times as additional expansion and contraction cycles may be necessary before clearing the obstruction.

Over the past several decades, several advances have been made in the field of balloon dilatation, and including use of visual and radiopaque markers at either a proximal or distal end of a sheath or an expandable balloon to improve centering about a target location. Such markers, while beneficial for getting the balloon dilator generally in the vicinity of an obstruction, may fail to place the balloon dilator at a geometric center of the obstruction. If the balloon is not placed at a geometric center of a stricture, the balloon is likely to migrate either distally or proximally during expansion of the balloon and the surgeon may have to deflate the balloon in order to re-center it about the stricture during the procedure. Use of markers that are not at a geometric center point of the balloon dilator may elongate procedure times unnecessarily.

Among the literature that can pertain to this technology include the following patent documents: U.S. Pat. Nos. 8,388,642 and 5,423,755, the entire contents of which are incorporated herein by reference for all purposes.

Despite the approaches discussed above, there is still a need for an endoscope device that allows for reliable visual verification of balloon positioning at a center point of a region of interest under endoscopic visualization prior to attempting inflation. In addition, there is a need for a device which provides reliable visual and fluoroscopic verification of balloon location about an area of interest to avoid patient injury and improve patient outcomes. It would be desirable to have a balloon dilator with a center marker which may be placed at a geometric center of a physiological obstruction. It would be desirable to reduce procedure time by reducing the number of expansions that were necessary to minimize an obstruction and effectively clear a passageway. It would be desirable to have a visual marker placed at a geometric center of a balloon. It would be desirable to have a balloon visual marker that selectively reflected certain wavelengths of light for positioning using endoscopes which selectively transmit certain frequencies of visible light.

SUMMARY OF THE INVENTION

The present invention is directed to an improved dilatation balloon catheter for the dilatation of the gastrointestinal tract. More specifically, the present invention meets one or more of the above needs by providing a dilatation balloon catheter that can be reliably placed about a center of a region of interest through the use of a single visual marker located at a geometric center point of dilatation balloon on the outer surface of a core wire (for the fixed wire balloon dilator) or on the outer surface of a sheath surrounding the core wire (for the wire guided balloon dilator).

A typical dilatation balloon consists of a distal end comprising a core member, or core wire, made of high strength material, such as stainless steel or a superelastic alloy such as nitinol, which extends through the inner lumen of a shaft and is secured directly or indirectly to a balloon. The proximal end of the core member is typically secured to a proximal portion of the catheter shaft or to a traction member at the proximal end of the catheter shaft. The distal end of the core member may be secured to the catheter shaft at either the proximal or distal ends of the balloon.

Some of the elements contributing to the improved dilatation balloon dilator construction include the type of material used in the fabrication of the dilatation balloon. In the present invention, the balloon material may be made of semi-compliant nylon and the catheter may be made of nylon. The balloon material may be substantially transparent, transparent, translucent, or a combination thereof, and allow for clear visualization of the visual marker which is contained inside the balloon. Further, the design incorporating the visual marker placed at a center point within the balloon on the core wire (fixed wire balloon dilator) or on the outer surface of a sheath surrounding the core wire (wire guided balloon dilator) contributes to the improved method for placement provided by the balloon dilator in the present invention.

A visual centering marker is provided to assist the user in optimally positioning the balloon for dilating a stricture or stenosis. The balloon may shift during inflation which may require repeat dilation attempts. Specifically for the case Where the balloon dilator is positioned slightly distal to the center point of the stricture, the balloon dilator would be likely to migrate or drift distally during inflation. Specifically for the case Where the balloon dilator is positioned slightly proximal to the center point of the stricture, the balloon dilator would be likely to migrate or drift proximally during inflation. The centering marker will ensure the balloon is properly positioned each time and may minimize repeat inflations and deflations.

The marker can be attached to, printed, or pad printed on an outer surface of the center core wire in the case of a balloon with an embedded wire. A center marker can also be added to the catheter in the wire guided balloon by attaching, printing, or painting a visual indicator on the outer surface of the catheter at a position corresponding to the balloon catheter center point.

The marker band may be used on a fixed wire or wire guided dilatation balloon configuration. For the fixed wire balloon, the dilation catheter may be used for dilation of strictures in the esophagus. For the wire guided balloon, the dilation catheter may be used for dilation of strictures in the gastrointestinal tract, including strictures of the esophagus, duodenum, pylorus, and colon. The fixed wire balloon catheters may be compatible with gastroscopes, whereas the wire guided balloon catheters may be compatible with both gastroscopes and colonoscopes.

The fixed wire tip may be a two-shot molded part with a pebax distal portion and a nylon proximal portion. The fixed wire balloon is intended to be used to dilate strictures in the esophagus. The fixed wire balloon catheters are typically compatible with gastroscopes.

The wire guided balloon catheter is intended to be used to dilate strictures in the GI tract, including strictures of the esophagus, duodenum, pylorus, and colon. The wire guided balloon catheters are typically compatible with both gastroscopes and colonoscopes.

Images may be captured by the endoscope as the balloon dilator extends therefrom. Using the center marker, a user may accurately place the balloon dilator at the center point of the area of interest for expansion.

Accordingly, pursuant to one aspect of the present invention, there is contemplated an apparatus, a balloon dilator, comprising an expandable balloon, a core wire which extends through the expandable balloon, and a single visual marker band positioned centrally within the balloon dilator.

The invention may be further characterized by one or any combination of the features described herein, such as the core wire extends through a sheath and, the core wire is movable with respect to the balloon and the balloon dilator is a wire guided balloon dilator, the single visual marker band is positioned on a sheath contained within the balloon dilator, the core wire is rigidly fixed to a distal end of the device and the balloon dilator is a fixed wire balloon dilator, the visual marker band is positioned on the core wire contained within the balloon dilator, an endoscope, the endoscope comprising a working channel through which the balloon dilator passes, the single visual marker band is 10 mm in length, the single visual marker band is pad printed onto the wire, a second visual marker band is positioned proximal to the proximal end of the expandable balloon on an outer sheath, a first radio-opaque marker band is placed distal to the distal tip of the expandable balloon and a second radio-opaque marker band is placed proximal to the proximal tip of the expandable balloon, the expandable balloon is configured to expand to three expansion diameters.

Pursuant to another aspect of the present invention, there is contemplated a method, comprising extending a balloon dilator through an endoscope, navigating the balloon dilator and endoscope through an anatomical passageway to a region of interest for clearing a stenosis, visualizing a position of a single visual marker to ensure the balloon dilator is initially positioned at a center point of the stenosis at a desired region, expanding the balloon dilator, monitoring the position of the visual marker during expansion to ensure the balloon dilator acts to effectively dilate the desired region.

The invention may be further characterized by one or any combination of the features described herein, such as the step of expanding the balloon dilator to three predetermined diameters and the step of monitoring the position of the visual marker during expansion to ensure the balloon dilator acts to effectively dilate the desired region, the balloon dilator further comprises at least a first radio-opaque marker band at a position distal to a distal balloon end and a second radio-opaque marker band proximal to a proximal balloon end, the step of verifying position of the balloon dilator with fluoroscopy.

Further aspects, advantages and areas of applicability will become apparent from the description provided herein. It should be understood that the description and specific examples are intended for purposes of illustration only and are not intended to limit the scope of the present disclosure.

DESCRIPTION OF THE DRAWINGS

The drawings described herein are for illustration purposes only and are not intended to limit the scope of the present disclosure in any way.

DETAILED DESCRIPTION OF THE INVENTION

The following description is merely exemplary in nature and is not intended to limit the present disclosure, application, or uses.

As will be seen, the devices and methods taught herein offer a visual marker band in the center of an expandable balloon for more precise placement of a balloon in the center of a target region.

Visual Marker

Structurally, it is contemplated that the visual marker band may extend a length in the range of 2 mm to 15 mm, preferably in the range of 5 mm to 10 mm, and most preferably in the range of 7 mm to 8 mm, the length extending from a distal end to a proximal end of the device. It is contemplated that the marker band may extend entirely around a circumference of the core wire or sheath, may extend around a partial circumference, may be visible from only one side of the balloon dilator, may be visible from both sides of the balloon dilator, or a combination thereof. The visual marker band may extend around an entire 360 degree circumference, may extend in the range of 270 degrees to 359 degrees around the circumference, may extend in the range of 180 degrees to 269 degrees around the circumference, or may extend less than 180 degrees around the circumference of the core wire or sheath. Additional visual marker bands may be provided, for example, on the catheter slightly proximal to the proximal end of the balloon or slightly distal to the distal end of the balloon. Radio-opaque marker bands may be located underneath one or more of the visual markers. Radio-opaque marker bands may be located in the distal tip, the proximal tip, or both, of the balloon to allow for ease of positioning under fluoroscopy. The marker may be attached to, printed, or pad printed on an outer surface of the center core wire in the case of a balloon with an embedded wire. The marker may be added to the catheter in the wire guided balloon by attaching, printing, or painting a visual indicator on the outer surface of the catheter at a position corresponding to the balloon catheter center point. The marker may comprise nylon, shrink tube, plastic, ink, or a combination thereof.

Functionally, the purpose of these marker bands would be to indicate to the user that the balloon has been advanced sufficiently beyond the face of the endoscope and that it is safe to begin inflation as well as to provide the ability to center the balloon about the geometric center of a stricture to prevent balloon migration. Functionally, the central visual marker may be phosphorescent, may reflect more brightly when hit with a particular wavelength, may carry a charge when exposed to light, may luminesce at a higher rate than white light. The marker band may be discernible through the folded balloon material prior to inflation and through the side wall of the balloon during and after inflation. The marker band may be provided with pigments, may be phosphorescent, may carry a charge after exposure to light (i.e. glow in the dark), may luminesce for certain frequencies at a higher rate than it would for white light, may have a reflective index of between 40 and 93 (Solar Reflectance Index), may reflect more brightly when hit with a particular wavelength of light, may have a spectral radiance for specific wavelengths, may have a smooth surface, may be configured for specular reflection, may have a rough surface, may be configured for diffuse reflection, or a combination thereof. The marker band may be fluorescent, may be iridescent, photoluminescent, chemiluminescent, electroluminescent, thermoluminescent, optically stimulated, may be provided with a surface that emits light when it has not been heated, may be capable of cold body radiation, or a combination thereof.

Functionally, use of a visual marker in conjunction with an endoscope would allow the user to be notified that the balloon has been advanced sufficiently beyond the face of the endoscope and that it is safe to begin inflation as well as to provide the ability to center the balloon about the geometric center of a stricture to prevent balloon migration.

Balloon

Structurally, the balloon, the catheter, or both may be comprised of semi-compliant nylon. The balloon material may be substantially transparent, transparent, translucent, or a combination thereof, and allow for clear visualization of the visual marker which is contained inside the balloon. Balloon length, measured from the distal most end of the balloon to the proximal most portion of the balloon, may be in the range of 20 mm to 90 mm, preferably 50 mm to 70 mm, most preferably between 55 mm to 66 mm. For more tortuous anatomy and/or strictures found in tortuous anatomical regions, a shorter balloon length may be desirable. For the wire guided balloon with balloon length of 65 mm, inflation diameter at the three inflation levels may be 6 mm, 7 mm, and 8 mm. For the wire guided balloon with balloon length of 65 mm, inflation diameter at the three inflation levels may be 8.5 mm, 9.5 mm, and 10.5 mm. For the wire guided balloon with balloon length of 55 mm, inflation diameters may be spaced equally in the range of 11 mm to 20 mm, or any subcombination thereof. For the fixed wire balloon with balloon length of 90 mm, inflation diameters may be spaced equally in the range of 6 mm to 10.5 mm, or any subcombination thereof. For the fixed wire balloon with balloon length of 80 mm, inflation diameters may be spaced equally in the range of 11 mm to 20 mm, or any subcombination thereof.

Functionally, the balloon may be in fluid communication with a proximal portion of the balloon dilator via an inner lumen such that the air pressure within the balloon may be increased to specific levels. One embodiment of the invention may include providing the balloon catheter with the ability to inflate to three specific diameters when the corresponding pressure is applied. The balloon dilator may be a two stage balloon dilator, a three-stage balloon dilator, or a four stage balloon dilator.

Fixed Wire Balloon Catheter

Structurally, the tip of the fixed wire may be a two-shot molded part with a pebax distal portion and a nylon proximal portion, for example. The core wire may be secured to an atraumatic distal tip at a distal end. The core wire may be secured to the tip using different mechanisms, including creation of a saw tooth, spiral, or other pattern in a distal region of the core wire that securely fixes the core wire into the atraumatic distal tip during molding.

Functionally, the tip of the fixed wire balloon catheter may be used to steer the balloon catheter into place. The rigidity provided at the tip and through the connection of the core wire into the tip may allow for this guidance to occur. Fixation of the core wire into the tip may ensure that the core wire maintains a fixed position in the tip upon reentry of the balloon catheter into the endoscope and removal of the balloon catheter from the patient.

Wire Guided Balloon Catheter

Structurally, the tip of the wire guided balloon catheter may be a pebax over-molded onto a nylon catheter, for example. In the wire guided balloon catheter, the core wire passes through a sheath to assist in guidance of the dilatation balloon catheter into position. The sheath may connect to a distal end of the balloon catheter and is provided with an atraumatic distal tip. Structurally, in the wire guided balloon catheter, a core wire may pass through a sheath to assist in guidance of the dilatation balloon catheter into position. The sheath may connect to a distal end and is provided with an atraumatic distal tip. A single visual marker band may be provided at the center point of the balloon.

Functionally, the wire guided balloon catheter allows the user to first advance a core wire into position and then extend the balloon catheter over the core wire. The wire guided balloon catheter may be compatible with a core wire that will come pre-loaded in the device. The core wire may be used to navigate tortuous anatomy to an area of interest and may allow the balloon catheter to extend into more tortuous anatomy or harder to reach areas. The core wire may have a diameter in the range of 0.01 cm to 0.20 cm, may preferably have a diameter in the range of 0.03 cm to 0.15 cm, and most preferably may have a diameter in the range of 0.08 cm to 0.09 cm.

Label

A label on the catheter, which may be glow-in-the-dark, phosphorescent, or a combination thereof, to ease viewing in an operating room with reduced lighting, may be provided on the catheter to identify the three target inflation diameters and pressure set points. It is contemplated that the balloons may be inflated with a 50%/50% contrast/saline mixture using an inflation device. The balloon may be inflated with any combination of contrast and saline, entirely contrast, or entirely saline.

Endoscope

Different endoscopes may be used for illumination of a target region in combination with a balloon dilator. Any endoscopic device that allows for reliable visual verification of balloon positioning at a center point of a region of interest under endoscopic visualization prior to attempting inflation may be used with the device of the present invention. For use in the gastrointestinal tract, a GI endoscope would be preferable. The endoscope may comprise a working channel through which the balloon dilator passes, a deflectable tip portion, and visualization.

The balloon dilator may be extended through an endoscope, the balloon dilator and endoscope may be navigated through an anatomical passageway to a region of interest for clearing a stenosis, a position of visual marker may be visualized to ensure the balloon dilator is initially positioned at a center point of the stenosis at a desired region, the balloon dilator may be expanded, and the position of the visual marker may be confirmed during expansion to ensure the balloon dilator acts to effectively dilate the desired region.

Narrow band imaging (NBI) is an optical imaging technology that enhances the visibility of vessels and other tissue on the mucosal surface, NBI works by filtering the white light into specific light wavelengths that are absorbed by hemoglobin and penetrate only the surface of human tissue. The shorter wavelengths only penetrate the top layer of the mucosa, while the longer wavelengths penetrate deep into the mucosa. NBI light is composed of just two specific wavelengths that are strongly absorbed by hemoglobin. As a result, with narrow band imaging, capillaries on the mucosal surface are displayed in brown and veins in the submucosa are displayed in cyan on the monitor. It is contemplated that pairing a visual marker that was selectively reflective for specific wavelengths with an endoscope which utilized narrow band imaging technology would be one way to maximize visualization of the visual marker prior to inflation through the collapsed balloon material as well as during and after inflation through a single layer of balloon material.

Core Wire

Structurally, a core wire may be secured to an atraumatic distal tip at a distal end in the fixed wire balloon dilator. The core wire may be secured using different mechanisms, including creation of a saw tooth, spiral, or other pattern in a distal region of the core wire that securely fixes the core wire into the atraumatic distal tip during molding.

In the fixed wire balloon dilator, the core wire s provided with a visual marker at a geometric center point of the balloon. The connection point of the core wire can be visualized under fluoroscopy as it connects to distal end.

In the wire guided balloon dilator, a void, or space in the sheath through Which the core wire may pass during insertion of the device into a region of interest is provided. The core wire may pass through the sheath to assist in guidance of the dilatation balloon catheter into position. The sheath connects to distal end and is provided with an atraumatic distal tip. One or more visual marker bands may be provided at the center point of the balloon on the surface of sheath.

Balloon Neck

Structurally, the balloon neck may be provided with a step down portion at one end of the balloon which tapers to the balloon opening.

Functionally, the balloon neck may include biasing means to urge an upper and lower portion of the balloon away from each other during expansion.

Balloon Opening

Structurally, in the fixed wire balloon dilator, the balloon opening is a point at Which the sheath surrounding the core wire terminates and only the core wire extends through the length of the balloon.

Functionally, the balloon neck is where inflation enters into the balloon and is withdrawn from the balloon.

Sheath

Structurally, the sheath is a polymer passageway fixed to an atraumatic distal tip in the wire guided balloon catheter and which extends to the proximal end of the balloon dilator for insertion of a core wire.

Functionally, the sheath serves as a passageway for the core wire to pass through to add in navigating torturous passageways during insertion. The outer surface of the sheath serves as a stationary surface upon which a visual marker may be placed at a geometric center of the balloon for visualizing prior to inflation as well as during and after inflation.

Figure 1:
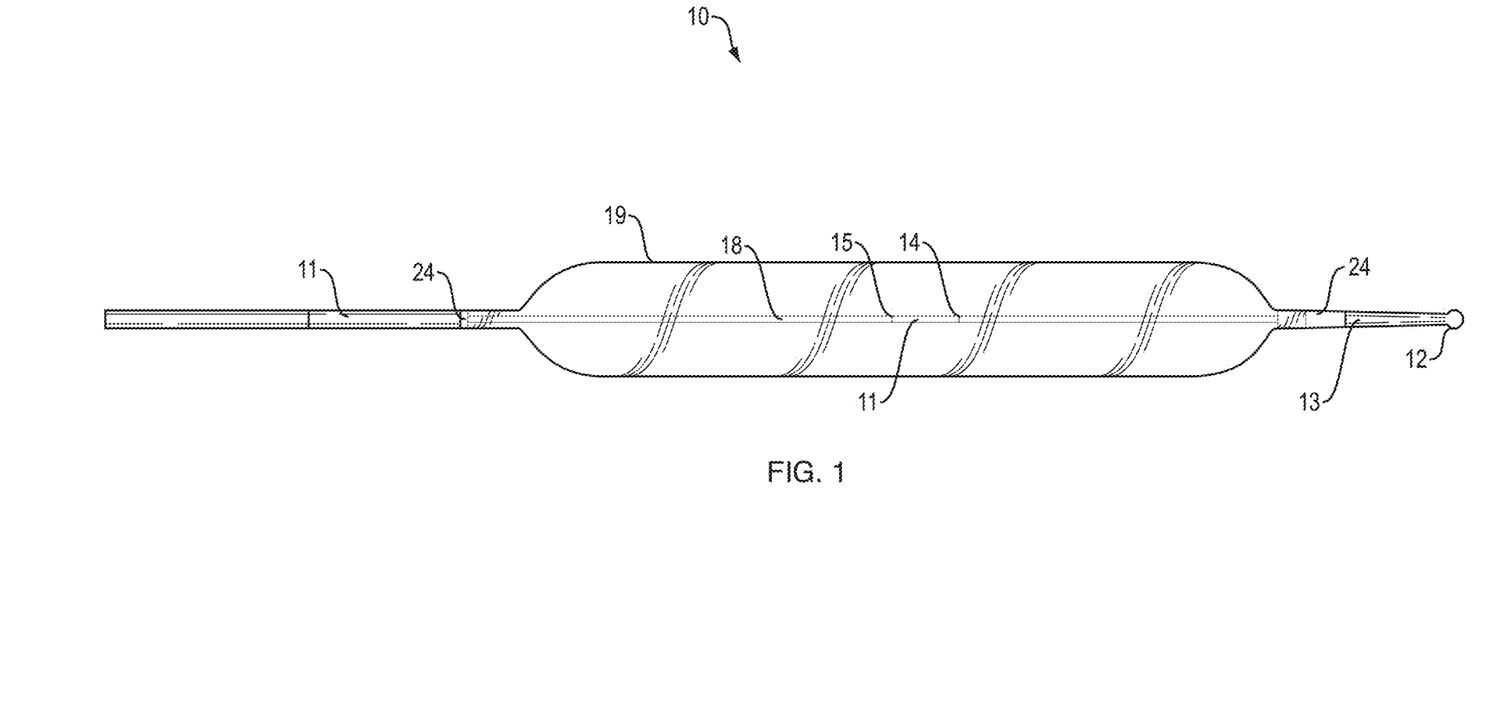
FIG. 1 is a side view of a fixed wire balloon dilatation catheter illustrating an aspect of the present invention.

Turning now to the drawings to illustrate examples of embodiments of the present teachings, FIG. 1 details side view of a distal end region of a fixed wire dilatation balloon. catheter 10. Core wire 18 is secured to atraumatic distal tip 12 at distal end 13. Core wire 18 may be secured using different mechanisms, including creation of a saw tooth, spiral, or other pattern in a distal region of the core wire that securely fixes core wire 18 into atraumatic distal tip during molding. A single visual marker band 11 is provided at the center point of balloon 19. Radio-opaque markers 24 are provided at both a proximal and distal end of balloon 19. Visual marker 11 provided at the center of balloon 19 is provided with a distal end 14 and a proximal end 15. The length of visual marker 11 can be determined by measuring the distance between distal end 14 and proximal end 15 of visual marker 11. Balloon 19 is shown in the frilly expanded state. It is contemplated that the ability to inflate to three specific diameters may help to maintain the balloon about the center point of the anatomical region of interest.

Figure 2:
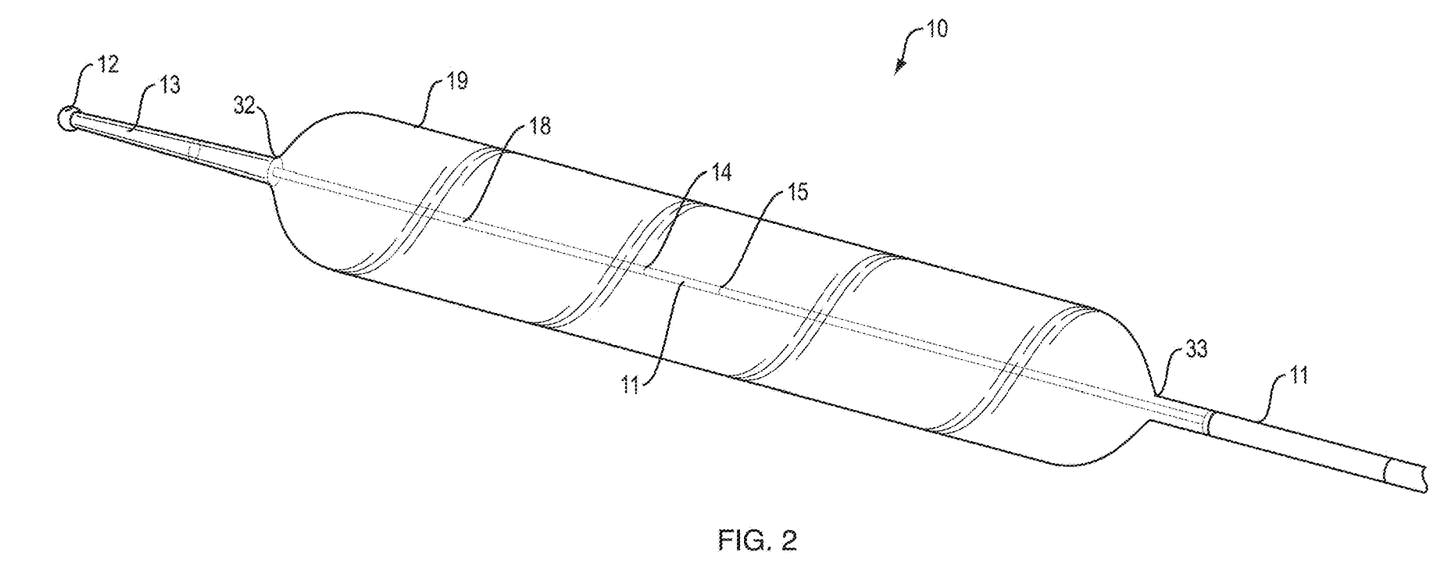
FIG. 2 is a perspective view of a fixed wire balloon dilatation catheter illustrating an aspect of the present invention.

FIG. 2 illustrates a perspective view of a distal end region of a fixed wire dilatation balloon catheter 10. The rounded distal portion 32 and rounded proximal portion 33 of balloon 19 can be clearly visualized here.

Figure 3:
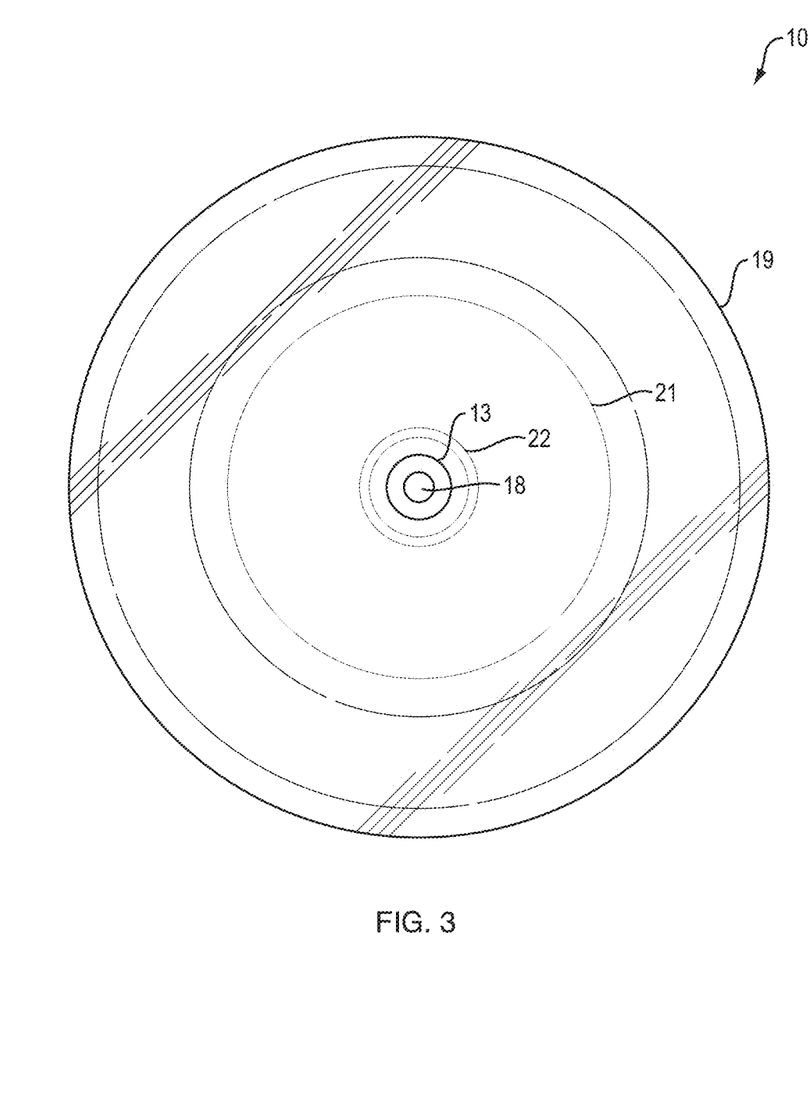
FIG. 3 is a cross sectional view along line A-A of FIG. 4 of a fixed wire balloon dilatation catheter illustrating an aspect of the present invention.
Figure 4:
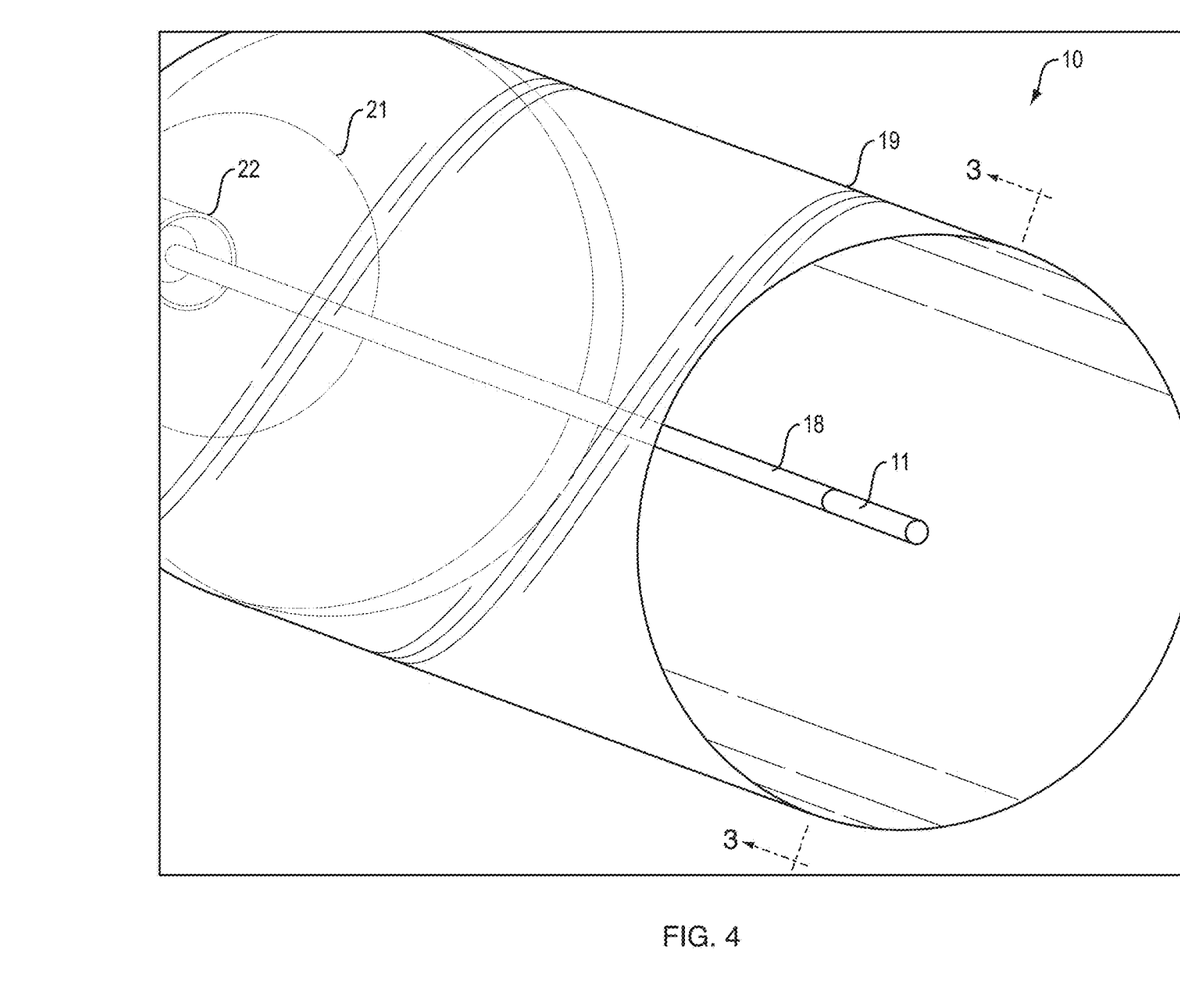
FIG. 4 is a partial perspective view of a fixed wire balloon dilatation catheter illustrating an aspect of the present invention.

FIG. 3 illustrates a cross sectional view of fixed wire balloon catheter 10 of along a line A-A in FIG. 4. Core wire 18 is surrounded by material from the atraumatic tip portion at distal end 13. The outer surface of balloon 19 can be visualized with a step down portion 21 at the balloon neck which tapers to balloon opening 22.

FIG. 4 illustrates a partial perspective view of fixed wire balloon catheter 10. Core wire 18 is provided with visual marker 11 at a center point of the balloon. The connection point of core wire 18 can be visualized as it connects to distal end 13. Balloon neck 21 is shown as a step down portion to balloon opening 22 of balloon 19.

Figure 5:
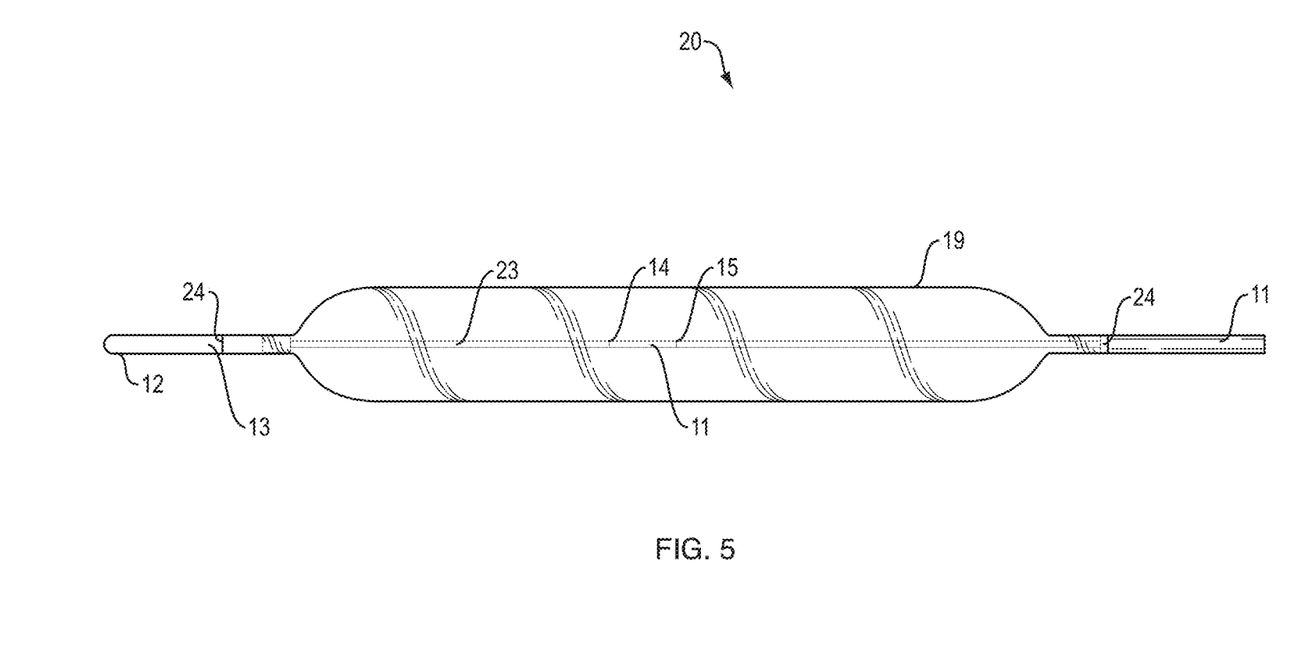
FIG. 5 is a side view of a wire guided balloon dilatation catheter illustrating an aspect of the present invention.

FIG. 5 illustrates a side view of a distal region of wire guided balloon catheter 20. Core wire 18 passes through sheath 23 to assist in guidance of the dilatation balloon catheter into position. Sheath 23 connects to distal end 13 and is provided with atraumatic distal tip 12. A single visual marker band 11 is provided at the center point of balloon 19 on the surface of sheath 23. Radio-opaque markers 24 are provided at both a proximal and distal end of balloon 19. Visual marker 11 provided at the center of balloon 19 is provided with a distal end 14 and a proximal end 15. The length of visual marker 11 can be determined by measuring the distance between distal end 14 and proximal end 15 of visual marker 11. Balloon 19 is shown in the frilly expanded state. It is contemplated that the ability to inflate to three specific diameters may help to maintain the balloon about the center point of the anatomical region of interest.

Figure 6:
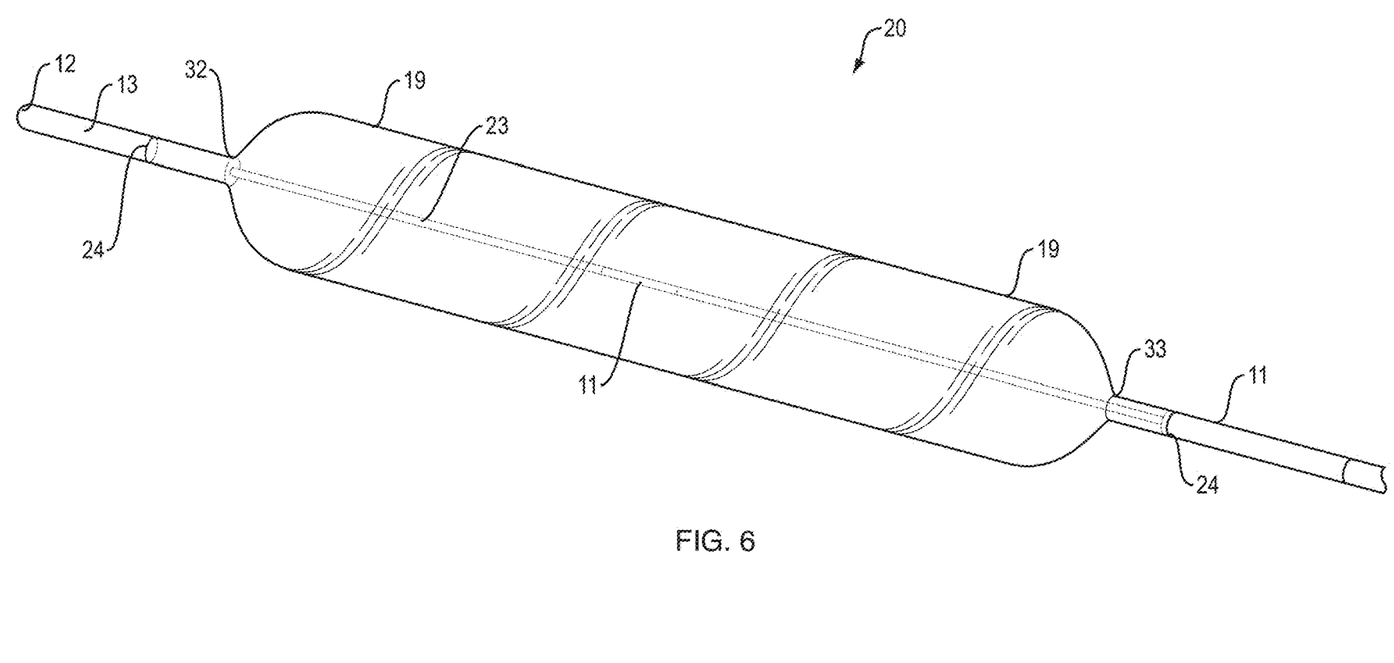
FIG. 6 is a perspective view of a wire guided balloon dilatation catheter illustrating an aspect of the present invention.

FIG. 6 illustrates a perspective view of a distal end region of a wire guided dilatation balloon catheter 20. The rounded distal portion 32 and rounded proximal portion 33 of balloon 19 can be clearly visualized here.

Figure 7:
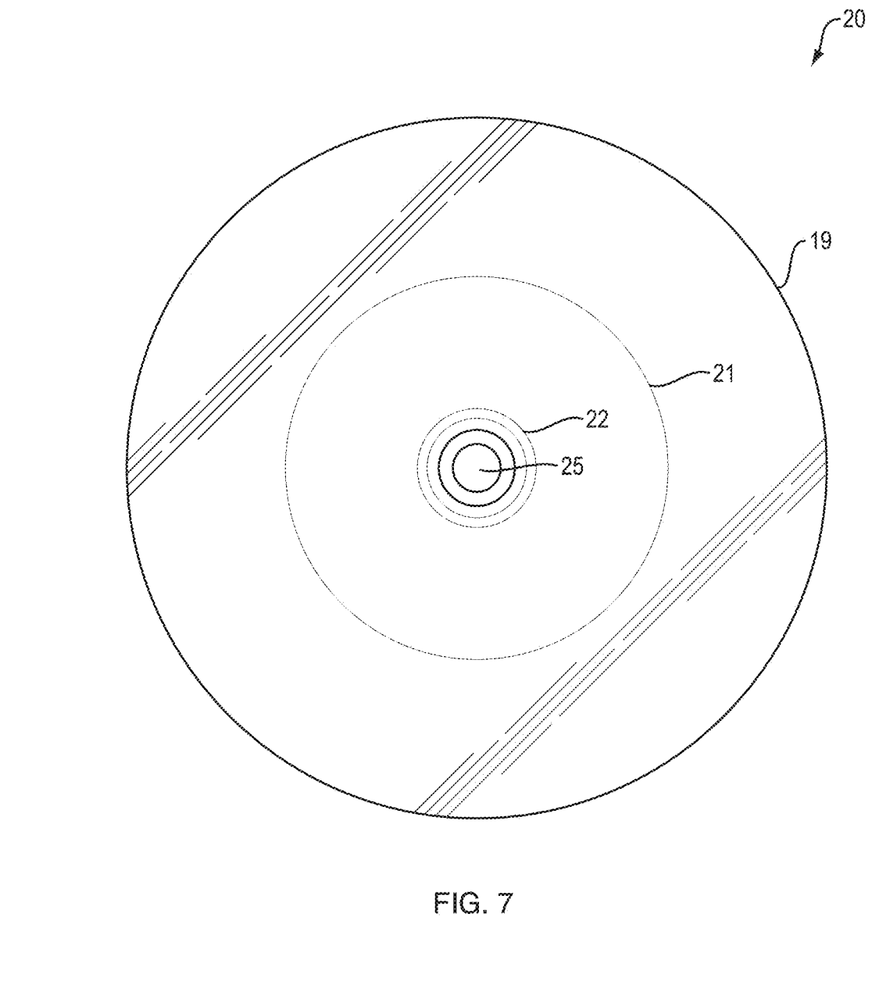
FIG. 7 is a cross sectional view along line B-B of FIG. 8 of a wire guided balloon dilatation catheter illustrating an aspect of the present invention.
Figure 8:
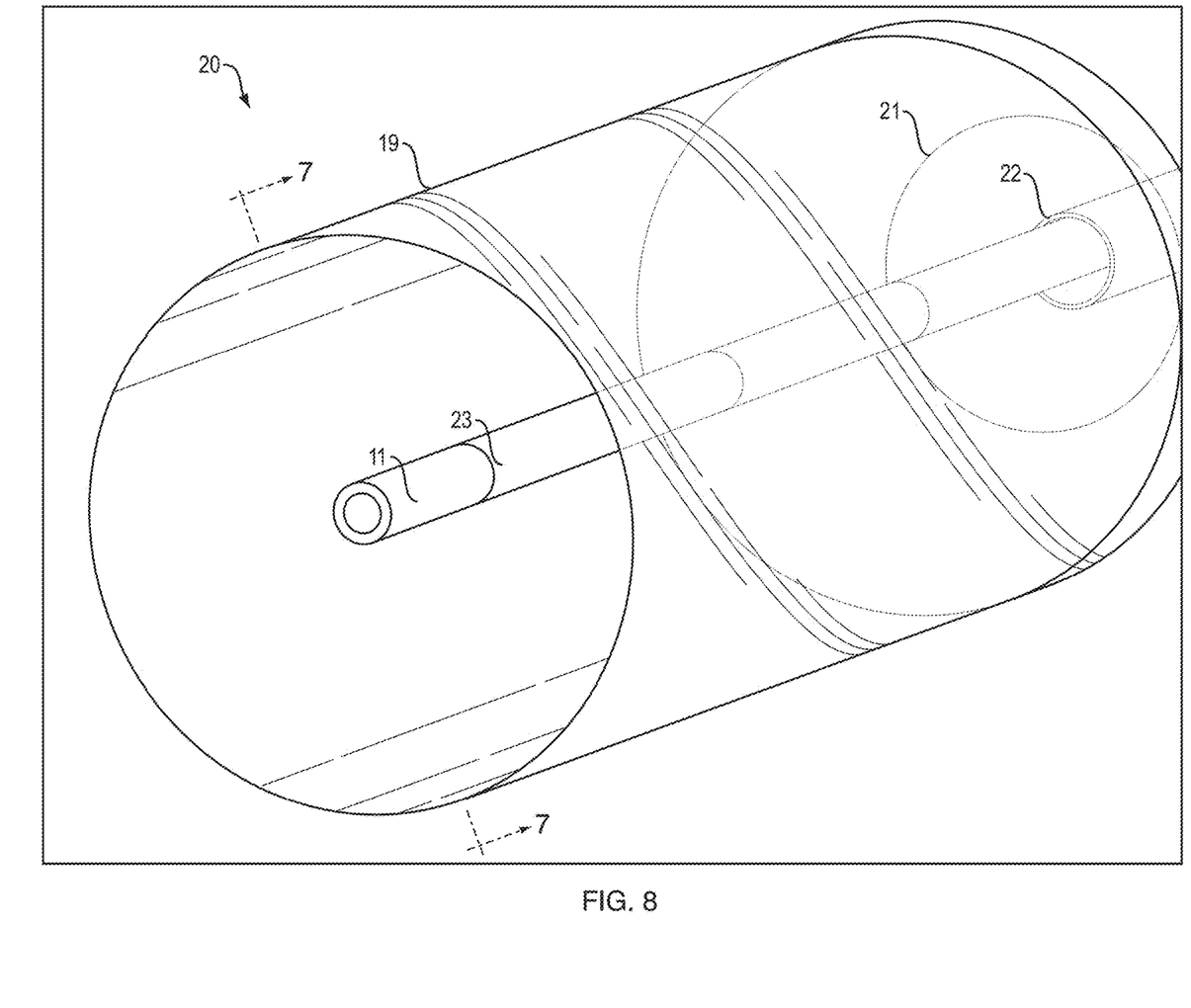
FIG. 8 is a partial perspective view of a wire guided balloon dilatation catheter illustrating an aspect of the present invention.

FIG. 7 illustrates a cross sectional view of wire guided balloon catheter 20 of along a line B-B in FIG. 8. Void 25 is a space through which core wire 18 may pass during insertion of the device into a region of interest. The outer surface of balloon 19 can be visualized with a step down portion 21 at the balloon neck which tapers to balloon opening 22.

FIG. 8 illustrates a partial perspective view of wire guided balloon catheter 20. Core wire 18 may pass through sheath 23 during insertion of the device. Sheath 23 is provided with visual marker 11 at a center point of the balloon. Balloon neck 21 is shown as a step down portion to balloon opening 22 of balloon 19.

Figures 9A, 9B:
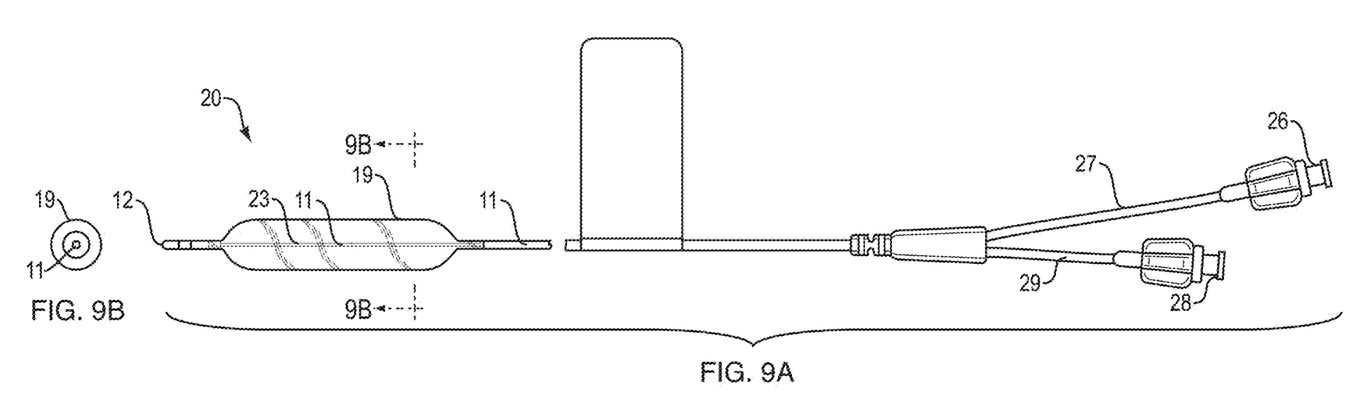
FIG. 9A is a side view of a wire guided balloon dilatation catheter illustrating an aspect of the present invention.
FIG. 9B is a cross sectional view along line 9B-9B of FIG. 9A of a wire guided balloon dilatation catheter illustrating an aspect of the present invention.

FIG. 9A illustrates a full side view of wire guided balloon dilator 20. Balloon 19 is shown in a fully expanded state with visual marker 11 placed at a center point of balloon 19 on sheath 23. An additional visual marker 11 is illustrated at a proximal region of the balloon dilator on an outer sheath. Atraumatic tip 12 is provided to ease potential injury to the patient during insertion. At the proximal end of the device, inflation port 26 provides an entry point for an expansion medium to enter via inflation lumen 27 into balloon 19. Additionally, core wire port 28 is provided at the proximal end of the device for entry of a core wire 18 through core wire lumen 29.

FIG. 9B illustrates a cross sectional view of wire guided balloon dilator 20. Balloon 19 is shown as surrounding visual marker 11. Visual marker 11 is positioned centrally within balloon 19.

Figure 10A:
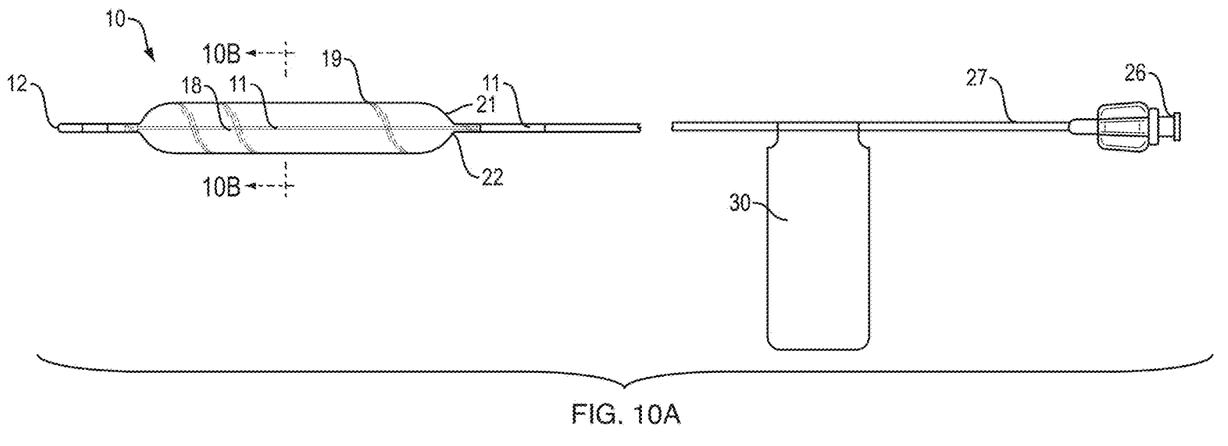
FIG. 10A is a side view of a fixed wire balloon dilatation catheter illustrating an aspect of the present invention.

FIG. 10A illustrates a full side view of fixed wire balloon dilator 10. Balloon 19 is shown in a fully expanded state with visual marker 11 placed at a center point of balloon 19 on core wire 18. An additional visual marker 11 is illustrated at a proximal region of the balloon dilator on an outer sheath. Atraumatic tip 12 is provided to ease potential injury to the patient during insertion. At the proximal end of the device, inflation port 26 provides an entry point for an expansion medium to enter via inflation lumen 27 into balloon 19.

Figure 10B:
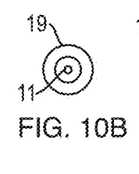
FIG. 10B is a cross sectional view along line 10B-10B of FIG. 10A of a fixed wire balloon dilatation catheter illustrating an aspect of the present invention.

FIG. 10B illustrates a cross sectional view of fixed wire balloon dilator 10. Balloon 19 is shown as surrounding visual marker 11. Visual marker 11 is positioned centrally within balloon 19.

Figure 11:
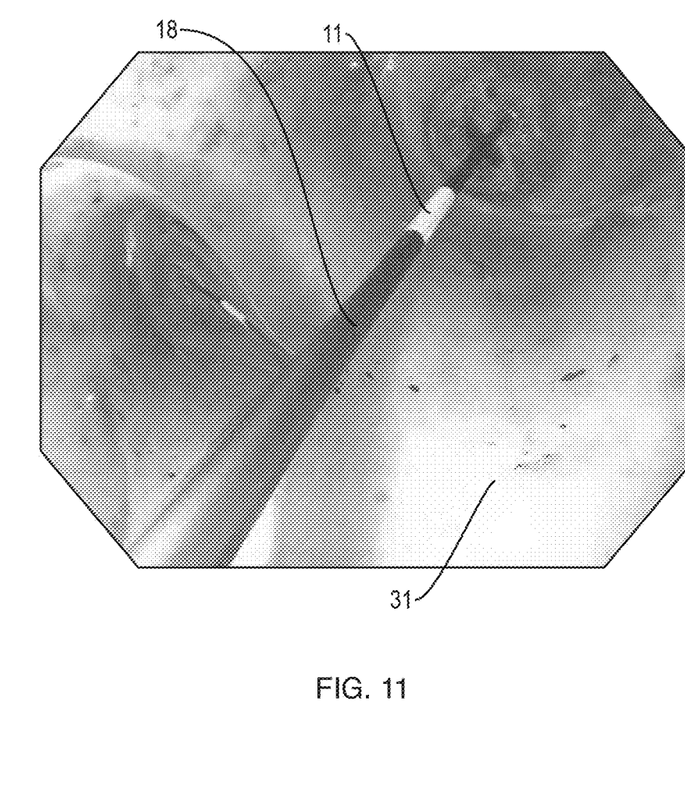
FIG. 11 is a perspective view of a wire guided balloon dilatation catheter illustrating the device of the present invention in use in a patient's anatomy.

FIG. 11 illustrates a perspective view through the side wall of balloon 19 in an anatomical region of interest 31. Visual marker 11, which is formed on core wire 18 is clearly visualized and can be positioned with ease about the anatomical region of interest 31.

ELEMENT NUMBERS

10 Fixed wire balloon catheter
11 Visual Marker
12 Atraumatic distal tip
13 Distal end
14 Distal end of visual marker
15 Proximal end of visual marker
18 Core Wire
19 Balloon
20 Wire Guided Balloon Catheter
21 Balloon Neck
22 Balloon Opening
23 Sheath
24 Radiopaque marker
25 Void
26 Inflation port
27 Inflation lumen
28 Core wire port
29 Core wire lumen/sheath
30 Label
31 Anatomy
32 Distal balloon end
33 Proximal balloon end

The invention claimed is:

1. A balloon dilator; comprising:
an expandable balloon;
a core wire that extends through the expandable balloon;
a single visual marker band positioned within the balloon dilator, the single visual marker band is positioned at a geometric center of the balloon between a distal tip of the expandable balloon and a proximal tip of the expandable balloon, and
a first radio-opaque marker band positioned distal to a distal tip of the expandable balloon and a second radio-opaque marker band positioned proximal to a proximal tip of the expandable balloon,
wherein the single visual marker band is selectively reflective for a specific wavelength of light that is used in narrow band imaging.

2. The balloon dilator of claim 1, wherein the single visual marker band is phosphorescent.

3. The balloon dilator of claim 1, wherein the single visual marker band comprises a rough outer surface.

4. The balloon dilator of claim 1, wherein the core wire extends through a sheath and, the core wire is movable with respect to the balloon and the balloon dilator is a wire guided balloon dilator.

5. The balloon dilator of claim 2, wherein the single visual marker band is positioned on a sheath contained within the balloon dilator.

6. The balloon dilator of claim 1, wherein the core wire is rigidly fixed to a distal end of the device and the balloon dilator is a fixed wire balloon dilator.

7. The balloon dilator of claim 4, wherein the single visual marker band is positioned on the core wire contained within the balloon dilator.

8. The balloon dilator of claim 1, further comprising an endoscope, the endoscope comprising a working channel through which the balloon dilator passes.

9. The balloon dilator of claim 1, wherein the single visual marker band is 10 mm in length.

10. The balloon dilator of claim 1, wherein the single visual marker band is pad printed onto the core wire.

11. The balloon dilator of claim 10, wherein the expandable balloon is configured to expand to three expansion diameters.

12. The balloon dilator of claim 8, wherein the endoscope is a narrow band imaging endoscope.

13. A method, comprising:
extending the balloon dilator according to claim 1 through an endoscope;

navigating the balloon dilator and the endoscope through an anatomical passageway to a region of interest;

visualizing a position of the single visual marker band through the endoscope;

expanding the balloon dilator;

monitoring the position of the single visual marker band during expansion.

14. The method of claim 13, further comprising a step of expanding the balloon dilator to three predetermined diameters.

15. The method of claim 13, further comprising a step of verifying position of the balloon dilator with fluoroscopy.

* * * * *